United States Patent [19]

McRae

[11] Patent Number: Plant 6,659

[45] Date of Patent: Mar. 7, 1989

[54] HYBRID ASIATIC LILY NAMED QUICKSTEP

[75] Inventor: Edward A. McRae, Boring, Oreg.

[73] Assignee: Melridge, Inc., Aurora, Oreg.

[21] Appl. No.: 80,497

[22] Filed: Jul. 31, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant having flowers particularly characterized by their vivid golden orange coloration, large size, broad tepals, and complete lack of spotting. The flowers are borne in large clusters and are of excellent form and long persistence and its color pattern and forcing period are completely new in the upright Asiatic divisions of lilies suited to forcing and to mass commercial production for the cut flower market.

1 Drawing Sheet

BACKGROUND OF THE NEW PLANT

This new variety of lily plant originated as a seedling selected from a group of seedlings planted by me at Sandy, Oreg., with seeds from a parent plant resulting from my crossing the clonal cultivar 'Connecticut King' (unpatented) with the clonal 'Croesus' (unpatented) as the pollen parent with the object of producing lilies in shades of gold and orange, well suited to forcing for cut flower production out-of-season. This particular seedling was selected by me because of the large size of its flowers which had broad tepals, a vivid gold-orange coloration, and a complete lack of spotting; a color pattern unique in this type of lily. This selected seedling was asexually reproduced by me and under my direction at Sandy, Oreg., and successive generations produced by bulb scale propagation and by natural propagation from bulblets have demonstrated that the novel and distinctive characteristics of this new variety are fixed and hold true, under asexual propagation, from generation to generation.

As observed at Sandy, Oreg., the clone of this new variety is vigorous and a good grower and propagator and it possesses to a high degree the desirable characteristics of hybrid vigor, great hardiness, and disease resistance; possessing in addition all of the desired characteristics of excellence of form, color and habit.

The new plant is well suited to forcing out-of-season when the bulbs are dug at the appropriate time and properly precooled; for example, October-dug bulbs, properly precooled and potted in January, will flower under glass in western Oregon in an average of eighty-four to ninety days, with no supplementary lighting and at moderate greenhouse temperatures.

DESCRIPTION OF THE DRAWING

This new variety of lily plant is illustrated by the accompanying photographic drawing which shows, in full color, an open bloom illustrating the flower form, the tepal arrangement, and the novel and distictive spotless, golden orange coloration; the colors shown being as close to those herein specified as can be obtained by professional photographic procedures.

DESCRIPTION OF THE NEW LILY VARIETY

The following is a detailed description of my new variety of Asiatic hybrid lily with nomenclature according to The International Lily Register, Second Edition, 1969, by The Royal Horticultural Society of London, England, the color designations being according to The R.H.S. Colour Chart published by the society in 1966.

THE PLANT

Origin: Seedling.

Parentage:

*Seed parent.*—Lilium 'Connecticut King' (unpatented).

*Pollen parent.*—Lilium 'Croesus' (unpatented).

Classification:

*Horticultural.*—Division IA, Upright Asiatic Hybrid Lily, according to The Horticultural Classification of Lilies by The Royal Horticultural Society of London.

*Commercial.*—Hybrid Lilum Clone.

Form: Single stem, erect and stately.

Height: About 80 to 100 cm. for stems produced by glasshouse forcing from bulbs of about 12 to 18 cm. in circumference with adequate light levels. Low light levels may cause "stretching".

Growth: Vigorous, sturdy and upright.

Foliage:

*Quantity.*—Abundant.

*Leaf size.*—About 6 to 12 cm. long and about 5 to 12 mm. wide.

*Leaf shape.*—Lanceolate with acuminate tip.

*Texture.*—Leathery.

*Aspect.*—Glossy.

*Color.*—Dark green, but slightly lighter on the under side.

Bulbs:

*Size.*—Various, ranging up to about 25 cm. in circumference in commercial use.

*Color.*—White.

THE BUD

Form: Long ovate with obtuse apex.

Size: About 8 to 9 cm. long and about 7 cm. in circumference just prior to opening.

Opening rate: The bud opens slowly, taking about one hour in response to morning light.

Color: Orange, 25B-C, at the center of the bud, slightly lighter at the apex and base, just prior to opening and as tepals unfurl.

Peduncle:

*Length.*—Averages about 4 to 6 cm., but may become longer if the light levels are too low or if the bulbs have been improperly stored prior to forcing.

*Color.*—Medium green overlaid with light plum.

THE FLOWER

Blooming habit: Once annually and profusely in midseason.

Size: The opened flower averages about 16 to 19 cm. in diameter.

Borne: In a single compact raceme having from nine to fourteen buds on a stem from a bulb of about 12 to 16 cm. in circumference.

Shape: Cup-shaped upon first opening and becoming flatter as the tepals recurve on the second day.

Tepalage;

*Number.*—Six.

*Arrangement.*—Hexagonal.

*Size.*—Outer tepals average about 3 cm. wide. The inner tepals average about 4 to 4.5 cm. wide and have entire and fluted margins.

*Shape.*—Ovate with acute tip.

*Appearance.*—Shiny.

*Color.*—The flowers are distinguished by the vivid golden orange coloring of the tepals. The base color is Orange, 25A-B, which deepens to 28B in an area about 1 cm. wide and about 2 cm. long at the center of each tepal and just above the nectaries. The nectaries are overlaid with white pubescence.

*Tepal spotting.*—The tepals are entirely unspotted.

*Persistence.*—The tepals stay on their stems for about three weeks.

Color changes: The flower may become slightly more orange and less gold as it ages, depending upon light levels. Usually there is only a slight change of color if the light levels are adequate for cut flower maintenance.

Pedicel:

*Length.*—Averages about 2 to 6 cm.

*Form.*—Sturdy and ascending up to about 60° from the horizontal.

*Color.*—Medium to dark green.

Fragrance: None.

Lasting quality: The flower is long lasting, about three weeks.

Disease resistance: The flower and plant are resistant to disease; in particular, to Fusarium Bulb Rot and Botrytis Blight.

THE REPRODUCTIVE ORGANS

Stamens:

*Number.*—Six.

*Arrangement.*—Typical of genus Lilium.

*Pollen and anthers (dehisced).*—Orange Red, 28A, in color.

*Filaments.*—Length: About 5 cm. Color: Soft Orange, 25C.

Pistil:

*Number.*—One.

*Length.*—About 5 cm.

*Stigma.*—Size: Medium, about 2 to 3 mm. wide. Color: Soft plum, Greyed Red, 180B-C.

Character of ovary: Typical of genus Lilium.

THE FRUIT

Fertility: The fruit is fertile.

Shape: Ovoid.

Color at maturity: Soft brown, sometimes overlaid with soft plum.

This new variety most closely resembles 'Croesus' but it has a deeper golden orange coloration at the center of the tepals, it is without any spotting, and it has a more compact inflorescence than does 'Croesus'. This new variety also resembles its sister seedlings 'Foxtrot' and 'Hornpipe'. With respect to 'Foxtrot', this new variety has longer stems, a deeper color, broader and less "clawed" tepals, a less recurved and more cup-shaped flower form, and it requires a longer forcing time. With respect to the variety 'Hornpipe', this new lily has darker and slightly shorter stems, shorter pedicels, a slightly higher bud count, narrower tepals having smooth rather than fluted tepal margins, and it requires a longer forcing time.

I claim:

1. The new and distinctive Asiatic hybrid lily plant and parts thereof, substantially as herein shown and described, characterized by its broad tepalled, unspotted, rich golden orange flowers, the excellence of its flower form, its vigorous growth, and its versatility both as a garden plant and as a cut flower variety particularly suited to forcing into flower out-of-season.

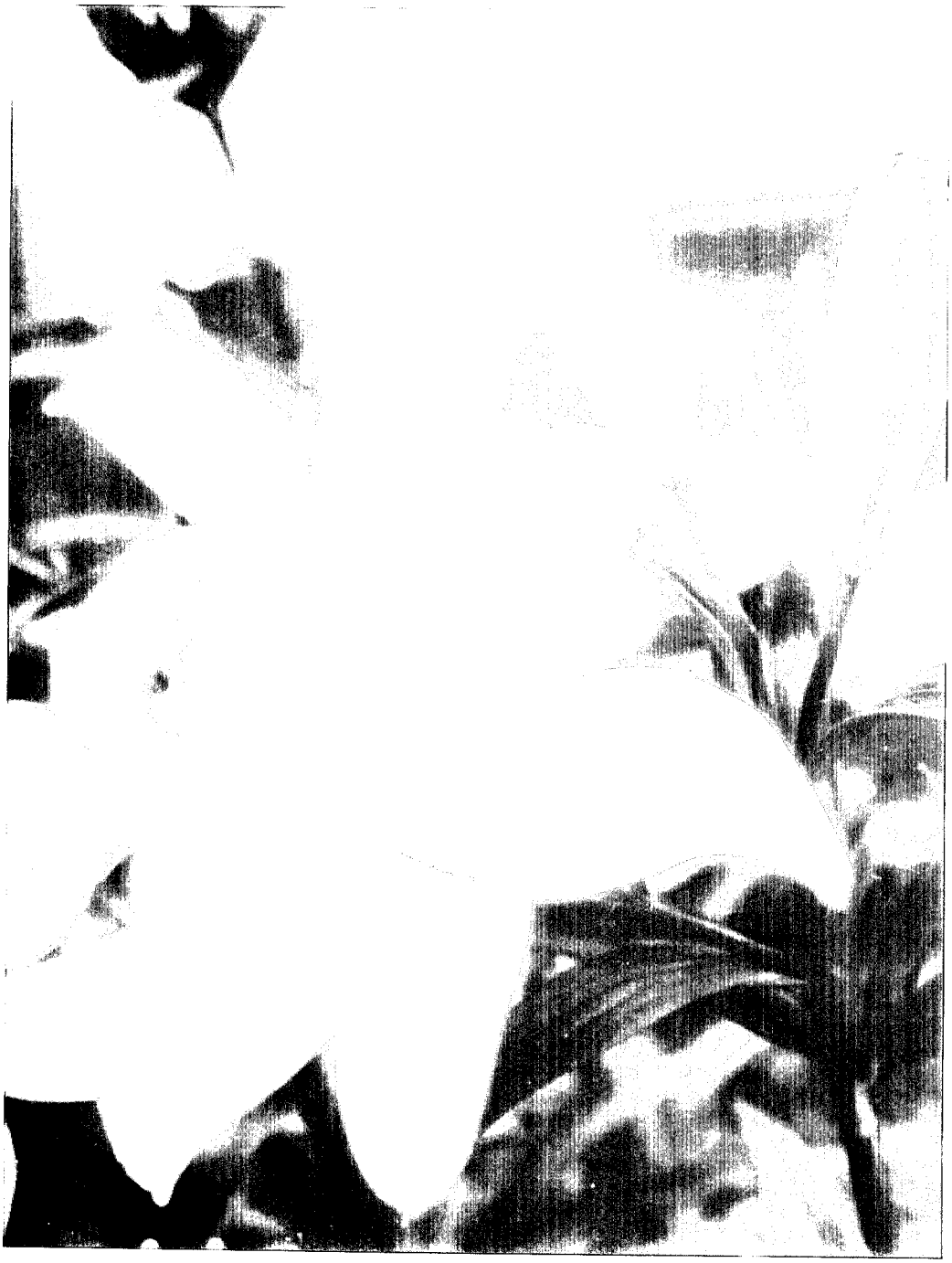

* * * * *